United States Patent [19]
Sakata et al.

[11] Patent Number: 5,264,369
[45] Date of Patent: Nov. 23, 1993

[54] METHOD OF PREPARING SPECIMEN FOR COUNTING SUBPOPULATIONS OF LEUKOCYTES AND ERYTHROBLASTS

[75] Inventors: Takashi Sakata; Mitsue Ito, both of Hyogo, Japan

[73] Assignee: TOA Medical Electrics Co., Ltd., Japan

[21] Appl. No.: 902,979

[22] Filed: Jun. 23, 1992

[30] Foreign Application Priority Data

Jul. 29, 1991 [JP] Japan .................. 3-188969

[51] Int. Cl.[5] .......................................... G01N 33/48
[52] U.S. Cl. ...................................... 436/63; 436/17; 436/172; 436/800
[58] Field of Search ................. 436/17, 63, 172, 800, 436/166, 174; 422/57

[56] References Cited

U.S. PATENT DOCUMENTS

| | | | |
|---|---|---|---|
| 3,906,120 | 9/1975 | Geating | 422/57 |
| 4,751,179 | 6/1988 | Ledis et al. | 436/63 |
| 4,978,624 | 12/1990 | Cremins et al. | 436/63 |
| 5,039,613 | 8/1991 | Matsuda et al. | 436/17 |
| 5,122,453 | 6/1992 | Martin et al. | 436/172 |

OTHER PUBLICATIONS

David Freifelder, "Molecular Biology", 1987 p. 713.
Frankel et al., "Gradwohl's Clinical Laboratory Methods and Diagnosis" 1970, p. 508.

Primary Examiner—James C. Housel
Assistant Examiner—Lien Tran
Attorney, Agent, or Firm—Pearne, Gordon, McCoy & Granger

[57] ABSTRACT

A hematological specimen for classifying and counting leukocytes with a flow cytometer is prepared. A sample to be assayed is prepared by eliminating influences of erythrocytes from a hematological sample without changing leukocytes morphologically by adding a first aqueous solution of a low osmotic pressure including a buffer for adjusting the pH value within an acidic region and a second aqueous solution including an osmolarity compensating agent and a buffer for giving pH value suitable for staining, optionally further adding a salt, which dissociates into ions in aqueous solutions so as to control the electrical conductivity of the aqueous solution at a preferable level, while damaging the cell membranes of erythroblasts contained in said sample; and staining the leukocytes with at least four dyes including Astrazon Yellow 3G and Neutral Red. Thus leukocytes contained in the hematological sample can be classified into at least eight groups including immature granulocytes, erythroblasts, basophils, eosinophils, lymphocytes, monocytes and neutrophils, or nine groups invoving one having blasts in addition to the above-mentioned eight groups, by assaying a single specimen with a flow cytometer.

7 Claims, 5 Drawing Sheets

METHOD OF PREPARING SPECIMEN FOR COUNTING SUBPOPULATIONS OF LEUKOCYTES AND ERYTHROBLASTS

BACKGROUND OF THE INVENTION

1. Field of the Invention

The present invention relates to a process for preparing a specimen for classifying and counting blood corpuscles in the practice of clinical testing. More particularly, it relates to a method for preparing a specimen to be used in classifying and counting leukocytes with a flow cytometer by means of optical or optical/electrical measurements on blood corpuscles.

2. Prior Art

Peripheral blood of normal subjects contains five types of leukocytes, namely, lymphocytes, monocytes, neutrophils, eosinophils and basophils.

These leukocytes differ from each other in function and, therefore, the classification and counting of leukocytes contained in the peripheral blood is highly useful in the diagnosis of various diseases.

It is well known that the peripheral blood of patients with, for example, leukemia, hemolytic anemia or cancer contains immature granulocytes, blasts and erythroblasts, which are usually observed not in the peripheral blood but in the bone marrow, in addition to the above-mentioned five types. These three blood corpuscles will be called "abnormal cells" hereinafter. Therefore, it is highly important to detect, classify and count these abnormal cells for diagnostic purposes.

Classification and counting of leukocytes have most commonly been accomplished by the differential counting method which is also referred to as the visual counting method or simply as the manual method. In this method, a blood sample is smeared on a glass slide and the blood corpuscles in the smear are fixed and stained for microscopic examination. The technician identifies the type of individual leukocytes according to their morphological features or the degree of dye uptake and thus performs classification and counting. In ordinary laboratories, 100 to 200 leukocytes are usually counted for each sample and the percentage of the total leukocyte count occupied by each type of corpuscle is recorded as a measured value.

The differential counting method has several disadvantages such that the preparation of the specimen to be examined requires troublesome procedures; that the classification through microscopic observation should be made by a skilled person and the measured value considerably varies from technician to technician; that the small number of leukocytes to be counted causes large statistical errors; and that it is a great burden for the technician to classify and count leukocytes by this method.

Therefore attempts have been made in order to automatically classify and count a number of leukocytes to thereby increase accuracy and save labor. Recently, automated devices based on a flow system for solving the above-mentioned problems have been marketed.

These automated devices may be roughly classified into the following three types depending on the measurement principle.

A device of the first type consists of three lysing agents and three types of detection units. In the first step, cells other than leukocytes contained in a blood sample are lysed with the first lysing agent and RF and DC signals of the remaining leukocytes are measured. Then the leukocytes are classified into three types, namely lymphocytes, monocytes and granulocytes depending on the difference in the signal intensity.

In the second step, cells other than eosinophils contained in the blood sample are lysed with the second lysing agent and the DC signals of the remaining cells are measured. Thus the eosinophils alone are classified and counted depending on the difference in the signal intensity.

The RF and DC signals will be now illustrated.

A direct current (DC) is applied between electrodes located at the both sides of a small aperture. Then a signal, which is produced due to a change in impedance upon the passage of a particle through the aperture, is referred to as a DC signal. On the other hand, a signal, which is produced due to a change in impedance upon the passage of a particle through the aperture when a radio-frequency (RF) current of several tens MHZ is applied between the electrodes, is referred to as an RF signal.

Needless to say, both of these currents may be applied simultaneously and thus both of the DC and RF signals can be detected.

In the third step, cells other than basophils contained in the blood sample are lysed with the third lysing agent and the DC signals of the remaining cells are measured. Thus basophils alone are classified and counted depending on the difference in the signal intensity.

Finally, the neutrophils are calculated by substracting the eosinophils determined in the second step and the basophils determined in the third step from the granulocytes determined in the first step.

A device of the second type consists of one lysing agent and one detection unit. As Japanese Patent Laid-Open No. 502533/1989 describes in detail, this method comprises treating a blood sample with a lysing agent whereby blood corpuscles other than leukocytes can be lysed without damaging leukocytes, measuring RF, DC and scattered light signals at the same time and then classifying and counting five types of leukocytes by appropriately combining the above-mentioned three signals.

A device of the third type consists of two agents and two detection units. In this method, blood corpuscles other than leukocytes contained in a blood sample are first lysed with a lysing agent and then subjected to peroxidase-staining with a dye solution. Next, the absorbance and scattered light signal of each leukocyte are measured and the leukocytes are classified and counted into four types (lymphocytes, monocytes, neutrophils and eosinophils) depending on the difference in the signal intensity. Then the blood sample is treated with another lysing agent capable of lysing blood corpuscles other than basophils. After measuring two types of scattered light signals, the basophils are classified and counted depending on the difference in the signal intensity.

The above-mentioned disadvantages of the manual method are solved by each of these automated methods. From the viewpoint of precision, in particular, a remarkable improvement has been achieved. Thus these automated methods are almost satisfactory in the practice of clinical testing.

However none of these methods makes it possible to specifically classify and count abnormal cells alone. Accordingly, there is a problem that a sample containing abnormal cells cannot be accurately analyzed or the presence of abnormal cells per se cannot be detected by these methods. In marketed devices, an abnormality in a scattergram due to the occurrence of abnormal cells is detected and a warning of, for example, abnormal or suspect flag is given so as to urge re-examination with the manual method by a technician, thus minimizing overlooking of abnormalities. In this case, however, the re-examination with the manual method is required, which means the object of labor-saving is not completely achieved.

Separately, there have been reported some methods whereby fluorescence or scattered light of each leukocyte in a fluorochrome-stained blood sample are measured with a flow cytometer so as to classify leukocytes. Major examples of these methods are described in Japanese Patent Publication No. 853/1984. Japanese Patent Laid-Open No. 20820/1975 and Japanese Patent Publication No. 70166/1988.

When a specimen, obtained by eliminating influences of blood corpuscles other than leukocytes from a hematological sample by an appropriate method, is assayed with a marketed flow cytometer as shown in FIG. 1, it is generally known that a scattergram as shown in FIG. 3 is obtained and the leukocytes are divided into three subpopulations respectively comprising lymphocytes 1′, monocytes 2′ and granulocytes 3′ mainly depending on the difference in the side scattered light intensity and each of these subpopulations can be easily classified and counted.

It is also possible, further, to divide the granulocytes into subpopulations comprising eosinophilis, basophils and neutrophils by combining the said process with the above-mentioned fluorochrome-staining. In Japanese Patent Laid-Open No. 134958/1988, we have already disclosed a method of dividing leukocytes into five subpopulations and classifying and counting each subpopulation with the use of a flow cytometer and reagents to be used in this method.

In Japanese Patent Laid-Open No. 134957/1988, we have further disclosed a method for classifying leukocytes into five types with the use of a combination of Neutral Red, which specifically stains eosinophils, with Astrazon Orange G, which specifically stains basophils. However, none of these methods makes it possible to specifically detect abnormal cells.

On the other hand, U.S. Pat. No. 4,500,509 discloses a manual method for classifying and counting leukocytes wherein all leukocytes including abnormal cell are fluorochrome-stained with Basic Orange 21 and then treated under a fluorescent microscope. However the above-mentioned disadvantages of the manual method cannot be solved by this method. Thus this U.S. patent provides no automated method.

SUMMARY OF THE INVENTION

As described above, the present invention aims at specifically detecting, classifying and counting abnormal cells, which cannot be achieved by conventional automated methods, and providing a method for preparing a specimen for flow cytometry in order to classify and count abnormal cells and to classify and count leukocytes involving abnormal cells.

The method for preparing a specimen according to the present invention may be roughly divided into two steps. In a first step, influences of erythrocytes contained in a hematological sample are eliminated in order to enable accurate measurement of scattered light intensity of leukocytes or scattered light intensity and cell volume. In a second step, leukocytes and erythroblasts are specifically stained.

Figure 1:
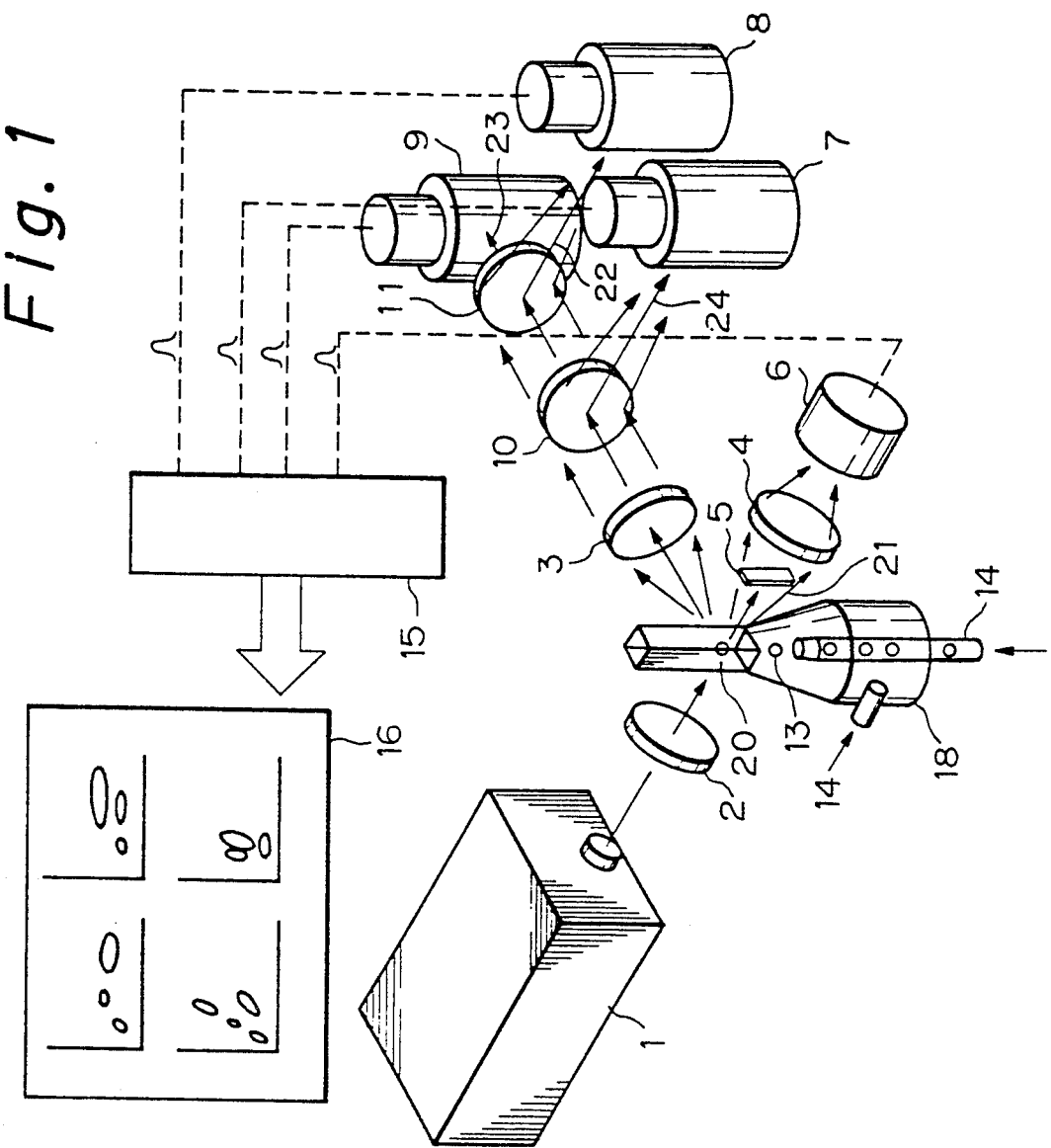
FIG. 1 is a schematic view showing the construction of a common flow cytometer.

In these figures, each symbol has the following meaning.

1: light source,
2: lens,
3: condenser lens
4: condenser lens,
5: beam stopper,
6–9: light detection units,
10–11: dichroic mirrors,
13: particle,
14: sheath fluid inlet,
15: signal-treatment unit,
16: analysis unit,
17: nozzle,
18: flow cell,
18a: orifice,
19: detection unit,
20: flow area of particle,
20a, b: electrodes,
21: forward scattered light,
22: red fluorescence,
23: green fluorescence,
24: side scattered light,
1′: lymphocytes,
2′: monocytes,
3′: granulocytes,
[NRBC]: erythroblasts,
[Eo]: eosinophils,
[A1]: subpopulation comprising leukocytes other than eosinophils and erythroblasts,
[A2]: subpopulation comprising blood corpuscles other than leukocytes,

[W1]-[W9]: windows 1-9
[Lym]: lymphocytes,
[Mono]: monocytes,
[Neut]: neutrophils,
[Ba]: basophils,
[Im1]: immature granulocyte group 1,
[Im2]: immature granulocyte group 2.
[Blast]: blasts
[Lym+blasts]: lymphocytes, blasts.

DETAILED DESCRIPTION OF THE INVENTION

In general, a hematological sample contains about 1,000 times as many erythrocytes as leukocytes. In flow cytometry, the intensity of a scattered light signal of lymphocytes is comparable to that of erythrocytes, which makes it difficult to separate lymphocytes from erythrocytes. As a result, accurate classification data of leukocytes can hardly be obtained. When a large number of erythrocytes pass through a detection unit of a flow cytometer simultaneously with leukocytes, furthermore, the scattered light signal of the leukocytes becomes less accurate and, therefore, it becomes difficult to separate lymphocytes, monocytes and neutrophils depending on side scattered light intensity. Alternately, cell volume cannot be measured with a device of the electrical resistance assay system in the presence of a large amount of erythrocytes. In order to solve these problems, it is required to eliminate erythrocytes in a hematological sample by some method.

In order to eliminate influences of erythrocytes without affecting the stain of leukocytes, a hematological sample is treated in the following manner. First, the hematological sample is treated under acidic and hypotonic conditions. Thus, the erythrocytes are converted into ghosts and then reduced into fragments. When the erythrocytes are completely lysed, the pH value and osmotic pressure are controlled each to a level causing no damage on leukocytes. Thus erythrocytes can be reduced into fragments without damaging leukocytes. As a result, the scattered light intensity of erythrocytes is reduced to a level corresponding to $\frac{1}{2}$ to $\frac{1}{3}$ of that of lymphocytes. Thus the simultaneous passage of erythrocytes with leukocytes is negligible in practice, furthermore the scattered light signal of leukocytes becomes accurate.

In order to assay blasts in a hematological sample, it is required to accurately measure cell volume based on the electrical resistance assay principle. The erythrocytes, which have been merely reduced into fragments, would pass simultaneously with leukocytes and thus make the leukocyte cell volume less accurate. In order to avoid this phenomenon, it is required to further reduce the size of the erythrocyte fragments. Thus, a step, wherein the fragmented erythrocytes alone are lysed with a nonionic surfactant, is further added.

A step for staining leukocytes and erythroblasts is based on the functions of four dyes. The specific staining characteristic of the present invention is based on the functions of three dyes. First, a hematological sample is fluorochrome-stained in the coexistence of Astrazon Yellow 3G and Neutral Red. Thus Astrazon Yellow 3G specifically stains basophils and immature granulocytes, while Neutral Red specifically stains eosinophils in red.

A third fluorochrome, capable of staining the nucleus of damaged cells exclusively, specifically stains the nuclei of erythroblasts the cell membranes of which have been lysed. A fourth dye, capable of staining at least the nuclei and cytoplasm of leukocytes, stains leukocytes which have not been stained with Astrazon Yellow 3G or Neutral Red or third fluorochrome. Thus these leukocytes can be separated from other blood corpuscles contained in the hematological sample depending on the difference in the intensity of fluorescene.

In usual measurement of optical parameters with a flow cytometer, it is not needed to control the electrical conductivity of a prepared specimen. When cell volume is to be measured based on the electrical resistance assay principle, however, it is required to adjust the electrical conductivity of a specimen to a level suitable for the measurement of the cell volume by the electrical resistance assay system. This can be achieved by adding an appropriate amount of salts which dissociate into ions in aqueous solutions.

The electrical conductivity suitable for the measurement of cell volume preferably ranges from 5 to 25 mS/cm, still preferably from 10 to 20 mS/cm.

The term "hematological sample" as used herein means a biological sample mainly comprising blood cells which is obtained from animal (in particular, human) peripheral blood or bone marrow punctate. A preferable example thereof is venous blood which has been treated with an anticoagulant. Further, a specimen obtained by previously eliminating blood corpuscles other than leukocytes from the above-mentioned hematological sample by a suitable method such as density gradient centrifugation may be preferably used in the present invention. The terms "lymphocytes", "monocytes", "neutrophils", "basophils" and "eosinophils" as used herein are identical with cells identified by the manual method by means of Romanovsky's stain which has been commonly employed in clinical testing.

Immature granulocytes consist of promyelocytes, myelocytes and metamyelocytes identified by the manual method. The above-mentioned two groups of immature granulocytes involve the immature granulocyte group 1 mainly comprising promyelocytes, in which the presence of primary granules (azure granules) is identified, and another group 2 mainly comprising myelocytes and metamyelocytes, in which few primary granules are identified.

The term "erythroblasts" as used herein means erythroid cells having a nucleus in cell.

The term "blasts" as used herein means the most immature cells of lymphocytes, monocytes and granulocytes and cells exceeding lymphocytes in size from among those assayed with the manual method.

A flow cytometer is a device by which at least three optical data (red fluorescence, green fluorescence, side scattered light), preferably four optical data (forward scattered light and the above-mentioned three factors) can be measured, as shown in FIG. 1. It is further preferable to use a flow cytometer as provided with an electrical resistance assay system (refer to FIG. 2) by which cell volume can be simultaneously measured.

The most preferable embodiment of the method of the present invention may be performed as follows. Namely, a hematological sample is mixed with a hypotonic and acidic first aqueous solution comprising:

(1) Astrazon Yellow 3G capable of specifically staining at least basophils and immature granulocytes;
(2) Neutral Red capable of specifically staining at least eosinophils;
(3) a dye capable of staining the nuclei of cells with damaged cell membranes;

(4) a dye capable of staining either or both of the nucleus and cytoplasm of leukocytes; and (5) a buffer in an amount sufficient for making the pH value of the aqueous solution acidic.

After erythrocytes are completely fragmentized and the cell membranes of erythroblasts are damaged and before the leukocytes are damaged, a second aqueous solution comprising:

(6) a buffer in an amount sufficient for neutralizing the acid in the first aqueous solution and adjusting the pH value to a level suitable for staining;

(7) an osmolarity compensating agent in an amount sufficient for adjusting osmotic pressure to a level suitable for maintaining leukocytes undamaged; and (8) a nonionic surfactant in an amount sufficient for lysing the erythrocytes fragments;

is added to thereby lyse the erythrocytes, followed by staining.

When the measurement of cell volume based on the electrical resistance assay principle is not performed, the component (8) is not always required.

The amount of Astrazon Yellow 3G sufficient for specifically staining basophils and immature granulocytes corresponds to 50 mg/l or above in the aqueous solution. It has been experimentally confirmed that the upper limit of the concentration of Astrazon Yellow 3G for achieving the effects of the present invention is 1,000 mg/l, though this does not mean that the effects of the present invention would disappear at a concentration exceeding the above-mentioned level.

The concentration of Neutral Red sufficient for specifically staining eosinophils corresponds to 1 mg/l or above in the aqueous solution. Still preferably, the concentration of Neutral Red ranges from 1/50 to 1/10 of the Astrazon Yellow 3G concentration. The staining with Astrazon Yellow 3G is competitive with the staining with Neutral Red and, therefore, an extremely high concentration of Neutral Red, compared with Astrazon Yellow 3G, would inhibit the specific staining of immature granulocytes with Astrazon Yellow 3G.

The above-mentioned dye capable of staining the nuclei of cells with damaged cell membranes means at least one fluorochrome selected from a group consisting of the following ones.

(1) ethidium bromide,
(2) propidium iodide,
(3) N-methyl-4-(1-pyrene)vinyl-pyridinium iodide.

The amount sufficient for staining the nuclei of cells with damaged cell membranes means such an amount sufficient for emitting fluorescence of an intensity by which erythroblasts can be separated from other cells in flow cytometry. The optimum concentration varies from dye to dye and thus should be determined through experiment. In the case of ethidium bromide, for example, a concentration of 10 mg/l or above is suitable.

The effects of these three dyes for staining the nuclei of cells with damaged cell membranes have been experimentally confirmed. However the present invention is not restricted thereto and any dye may be used so long as it can exclusively stain the nuclei of cells with damaged cell membranes.

The above-mentioned dye capable of staining either nuclei or cytoplasm or both of these substances means at least one fluorochrome selected from a group consisting of the following dyes.

(1) Astrazon Orange R (CI No. 48,040, CI Basic Orange 22)
(2) Astra Violet (CI No. 48070, Basic Red 12)
(3) Rhodamine 6G (CI No. 45160)
(4) Rhodamine 19
(5) Rhodamine B (CI No. 45170, Basic Violet 10)
(6) Rhodamine 3GO (CI No. 45210, Basic Red 3)
(7) Pyronine B (CI No. 45010)
(8) Cyanosine
(9) 3,3'-dimethylthiocarbocyanine iodide
(10) 3,3'-diethylthiocarbocyanine iodide
(11) 3,3'-dipropyloxacarbocyanine iodide
(12) 3,3'-dihexyloxacarbocyanine iodide
(13) 3,6-bis(dimethylamino)-10-dodecylacridinium bromide
(14) 7-benzylamino-4-nitrobenzoxadiazole
(15) 7-fluoro-4-nitrobenzoxadiazole
(16) Astrazon Red 6B (CI No. 48020, Basic Violet 7).

The amount sufficient for staining either or both of the nuclei and cytoplasm of leukocytes means such an amount sufficient for emitting fluorescence of an intensity by which leukocytes can be separated from other cells in flow cytometry. The optimum concentration varies from dye to dye and thus should be determined through an experiment. In the case of Astrazon Orange R, for example, a concentration of 100 mg/l or above is suitable. The effects of these 16 dyes have been experimentally confirmed by us. However the present invention is not restricted thereto and any dye may be used so long as it satisfies the above-mentioned requirements.

The acidity of the first aqueous solution may preferably fall within a pH range of from 2.0 to 4.0, still preferably from 2.0 to 3.5. The buffer to be used in the first aqueous solution is not particularly restricted. It is recommended to use a buffer having a pKa of 3.0±2.0. The buffer is used at a concentration suitable for maintaining the pH value of the mixture at 2.0 to 4.0. The concentration preferably ranges from 5 to 50 mM/l.

When the pH value is lower than 2.0, the staining of leukocytes is evidently inhibited. When the pH value exceeds 4.0, on the other hand, the fragmentation of erythrocytes is evidently inhibited. The term "hypotonic" means an osmotic pressure of 100 m Osm/kg or below. When the osmotic pressure exceeds 100 m Osm/kg, the fragmentation of erythrocytes is evidently inhibited.

The reaction time between the first solution and the hematological sample required for completely reducing erythrocytes into fragments somewhat depends on temperature. At room temperature (18° to 25° C.), it is completed within 5 to 20 seconds. The reaction time is somewhat shortened at a higher temperature and somewhat prolonged at a lower temperature.

The mixing ratio by volume of the hematological sample to the first aqueous solution is not particularly restricted. In the measurement with a flow cytometer, a mixing ratio ranging from 1:5 to 1:200 is preferable.

The pH value suitable for staining means from pH 7.0 to 11.0, still preferably from 7.5 to 10.0. When the pH value is lower than 7.0, the effects of specifically staining basophils and immature granulocytes can be hardly achieved. When the pH value exceeds 11.0, on the other hand, leukocytes are liable to be damaged.

The buffer to be used in the second aqueous solution is not particularly restricted. It is recommended to use a buffer having a pKa of 9.0±2.0. The concentration of the buffer is not particularly restricted and preferably ranges from 5 to 100 mM/l.

The time required for completing the staining somewhat depends on temperature. At room temperature (18° to 25° C.), it is completed within 10 to 40 seconds.

The reaction time is somewhat shortened at a higher temperature and somewhat prolonged at a lower temperature.

In order to limit damage to leukocytes and maintain at least lymphocytes, monocytes and neutrophils in a shape required for separation depending on scattered light, it is advantageous that the osmotic pressure of the mixture ranges from 100 to 500 mOsm/kg, still preferably from 200 to 400 mOsm/kg. When the osmotic pressure of the mixture does not fall within this range, it is recommended to add an osmolarity compensating agent to the aqueous solution. The type of the osmolarity compensating agent is not particularly restricted. It is preferable to use substances commonly employed for maintaining biological cells at physiological osmotic pressure (for example, alkali metals and saccharides) therefor. When cell volume is to be measured with a flow cytometer provided with an electrical resistance assay system, it is preferable to control the electrical conductivity of the finally prepared specimen. It is generally advantageous to adjust the electrical conductivity of said specimen to the same level as that of the sheath fluid.

Usually, the buffers contained in the fist or second solution dissociate into ions so as to give an appropriate electrical conductivity, which makes the adjustment unnecessary. However it is preferable to add salts, which dissociate into ions in aqueous solutions and thus impart electrical conductivity thereto, to the second solution to thereby adjust the electrical conductivity to a level suitable for measuring cell volume. Alkali metal salts may be preferably employed for this purpose, though the present invention is not restricted thereto.

The nonionic surfactant for lysing fragmented erythrocytes is a surfactant having polyoxyethylene in hydrophilic group in the molecular structure. It is preferable to use those having an average degree of polymerization of polyoxyethylene of 20 or more, still preferably 25 or more. A surfactant of an average degree of polymerization less than 20 is scarcely usable since it might damage leukocytes.

The nonionic surfactant may be added to either or both of the first and second aqueous solutions. It is preferable to add the same to the second aqueous solution alone.

Now structures of the dye to be used in the method of the present invention will be given.

Astrazon Yellow 3G (CI No. 48,055, CI Basic Yellow 11)

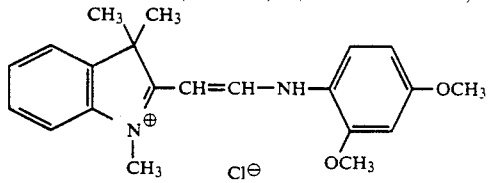

Neutral Red (CI No. 50,040, CI Basic Red 5)

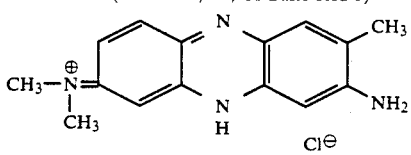

Astrazon Orange R (CI No. 48,040, CI Basic Orange 22)

Astrazon Violet (CI No. 48,070, Basic Red 12)

Rhodamine 6G (CI No. 45,160)

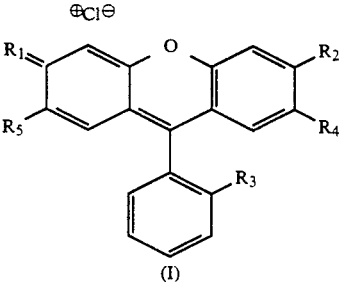

In formula (I), $R_1$: $=N^+HC_2H_5$,
$R_2$: $-NH-C_2H_5$,
$R_3$: $-COOC_2H_5$,
$R_4, R_5$: $-CH_3$.

Rhodamine 19

In formula (I), $R_1$: $=N^+H-C_2H_5$,
$R_2$: $-NH-C_2H_5$,
$R_3$: $-COOH$,
$R_4, R_5$: $-CH_3$.

Rhodamine B (CI No. 45,179, Basic Violet 10)

In formula (I), $R_1$: $=N^+H_2$,
$R_2$: $-NH_2$,
$R_3$: $-COOCH_3$,
$R_4, R_5$: $-H$.

Rhodamine 3GO (CI No. 45,210, Basic Red 3)

In formula (I), $R_1$: $=N^+H-CH_3$,
$R_2$: $-NH_2$,
$R_3$: $-COOCH_3$,
$R_4$: $-CH_3$,
$R_5$: $-H$.

Pyronine B (CI No. 45,010)

Cyanosine

-continued

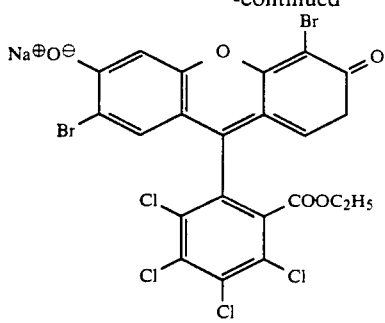

3,3'-Dimethylthiocarbocyanine iodide

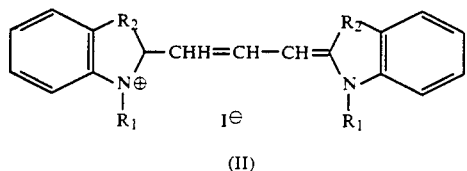

(II)

In formula (II), $R_1$: —$CH_3$,
$R_2$: —S—.

3,3'-Diethylthiocarbocyanine iodide
In formula (II), $R^1$: —$C_2H_5$,
$R_2$: —S—.

3,3'-Dipropyloxacarbocyanine iodide
In formula (II), $R_1$: —$C_3H_7$,
$R_2$: —O—.

3,3'-Dihexyloxacarbocyanine iodide
In formula (II), $R^1$: —$C_6H_{13}$,
$R_2$: —O—.

3,6'-Bis(dimethylamino)-10-dodecylacridinium bromide

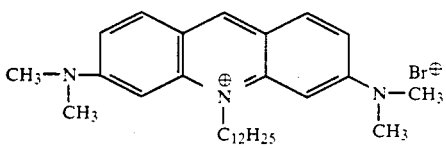

7-Benzylamino-4-nitrobenzoxadiazole

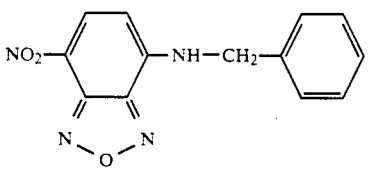

7-Fluoro-4-nitrobenzoxadiazole

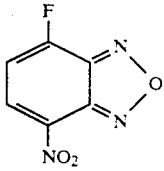

Astrazon Red 6B (CI No. 48,020, Basic Violet 7).

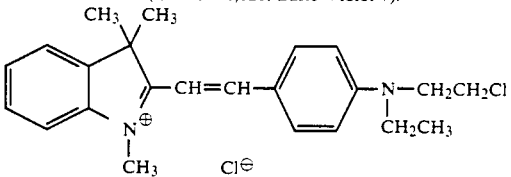

-continued

Ethidium bromide

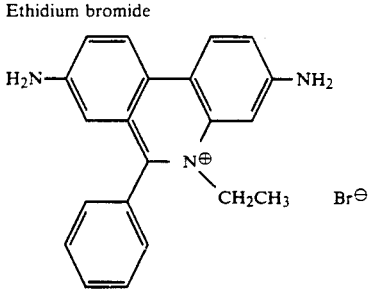

Propidium iodide

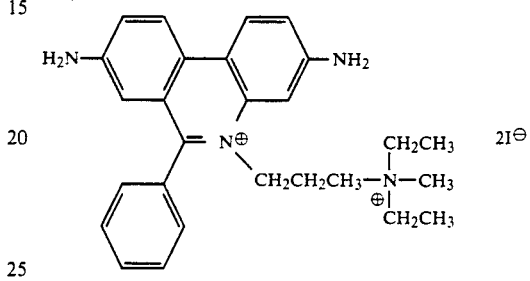

N-methyl-4-(1-pyrene)vinylpyridium iodide.

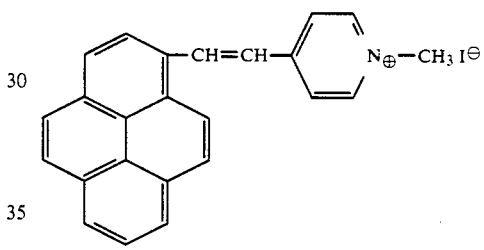

Now, a flow cytometer to be used in the embodiment of the present invention will be illustrated. FIG. 1 is a schematic diagram showing the construction of a common flow cytometer. In FIG. 1, 1 is a light source of the flow cytometer from which light of a wavelength suitable for exciting the specific fluorescence at least from eosinophils, basophils and immature granulocytes stained with Astrazon Yellow 3G and Neutral Red is emitted. As this light source 1, an argon ion laser or a mercury arc lamp capable of emitting light of 400 to 520 nm in wavelength may be preferably used. The light from the light source is condensed in a flow area 20 of particles by a lens 2 in the form of a flat circle and a particle 13 (cell etc.) passing therethrough is irradiated therewith. Thus forward scattered light 21 is emitted forward from the particle 13, while red fluorescence 22, green fluorescence 23 and side scattered light 24 are emitted sideways from the same.

The particles are discharged from a nozzle 17, enveloped in a sheath fluid supplied from a sheath fluid inlet 14, and then form a sheath flow in a flow cell. Direct light is removed from the forward scattered light 21 with a beam stopper 5 and the scattered light is transported to a light detection unit 6 via a condenser lens 4.

On the other hand, the lights 22, 23 and 24 emitted sideways are transported to light detection units via a condenser lens 3.

The side scattered light 24 is reflected upon a dichroic mirror 10 and then transported to a light detection unit 7.

The red fluorescence 22 is reflected upon a dichroic mirror 11 and transported to a light detection unit 8.

The green fluorescence 23 passes through a dichroic mirror 11 and is transported to a light detection unit 9.

Then the lights transported to the light detection units 6, 7, 8 and 9 are respectively converted into electric signals which are amplified in a signal treatment unit 15 and analyzed in an analysis unit 16.

The term "forward scattered light" to be used herein means scattered light emitted from a cell passing through the detection unit at a narrow angle of almost 0° based on the emission axis of the light source. The term "side scattered light" as used herein means scattered light emitted from a cell to be detected at an angle of almost 90° based on the emission axis of the light source. The term "red fluorescence" means fluorescence of a wavelength of 560 nm and above from among those emitted in all directions from a cell. Fluorescence at almost 0° or 90° from the emission axis of a light source can be condensed with a usual flow cytometer.

The term "green fluorescence" means fluorescence of a wavelength around 520 to 560 nm from among those emitted in all directions from a cell. Fluorescence at almost 0° or 90° from the emission axis of a light source can be condensed with a usual flow cytometer.

Figure 2:
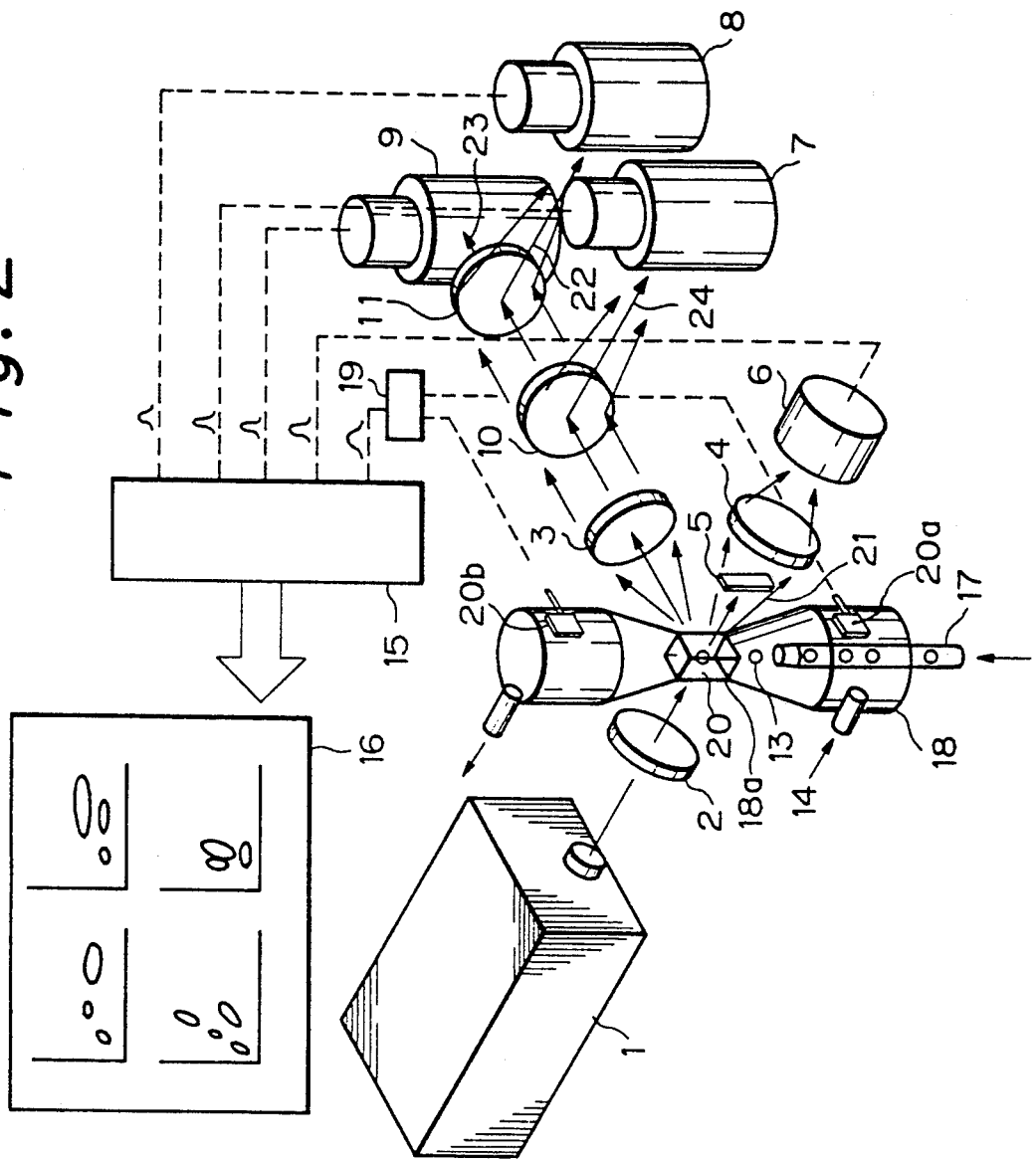
FIG. 2 is a schematic view of a flow cytometer to be used in the method of the present invention by which optical signals and electric resistance signals can be measured simultaneously.
Figure 3:
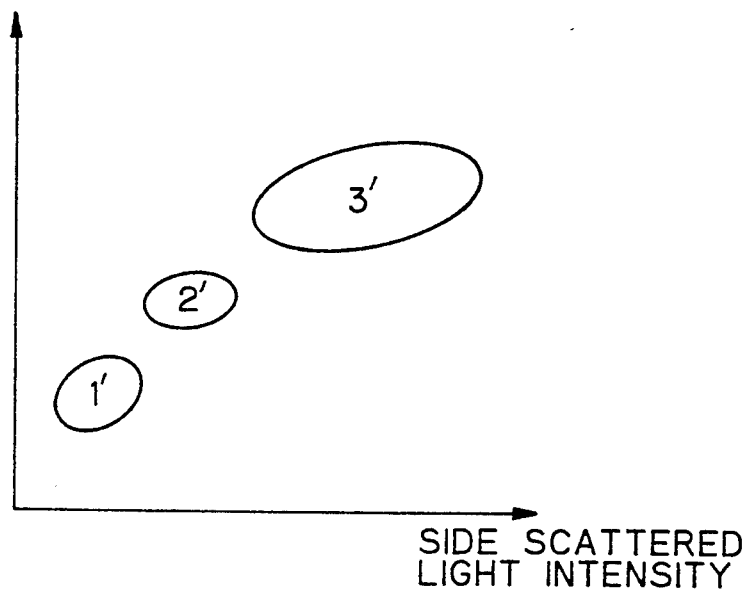
FIG. 3 is a scattergram obtained by measuring a specimen, which is prepared by eliminating influences of blood corpuscles other than leukocytes from a hematological sample, with the flow cytometer shown in FIG. 1.

FIG. 2 is a schematic diagram of a flow cytometer to be used in the present invention by which optical signals and electrical signals can be simultaneously measured. Optical signals can be detected by the same method as the one described regarding FIG. 1. On the other hand, electrical signals can be detected as follows. A flow cell 18 is provided with an orifice 18a for measuring electrical resistance. Light emitted from the light source 1 is condensed around the center of the orifice 18a with a lens 2. As is well known, the accurate volume of a cell of a certain size can be determined by measuring a change in electrical resistance between electrodes 20a and 20b due to the passage of the cell through the orifice 18a. In the present invention, the electrical signals and optical signals can be simultaneously detected.

Similar to the detection of optical signals, a specimen is introduced into the cell 18 via the nozzle 17. The sheath fluid is supplied from the sheath fluid inlet 14 and thus a laminar flow is formed in the flow cell 18. Particles 13 pass thorough the orifice 18a one by one. At this moment, an electrical signal based on the electrical resistance principle and the optical signal can be simultaneously obtained.

The electrical signal detected based on the electrical resistance principle is then converted into an electrical pulse signal having a height corresponding to the volume of the cell in the detection unit 19. Signals respectively detected in the units 6, 7, 8, 9 and 19 are amplified in the signal treatment unit 15 and then analyzed in the analysis unit 16.

EXAMPLES

Now, the treatment steps of the present invention will be described by reference to particular examples. Reagents used in these examples were prepared from marketed chemical materials of reagent grade.

EXAMPLE 1

Composition Example 1

| First reagent solution: | |
| --- | --- |
| Astrazon Yellow 3G | 300 mg |
| Neutral Red | 20 mg |
| ethidium bromide | 50 mg |
| Astrazon Orange R | 300 mg |
| citric acid monohydrate | 2.10 g (pH 2.62) |
| purified water (pH: 2.62, osmotic pressure: about 10 mOsm/kg). | 1 l |
| Second reagent solution: | |
| taurine | 37.5 g |
| NaCl | 58.4 g |
| NaOH | 16.0 g |
| purified water | 1 l |

Figure 4:
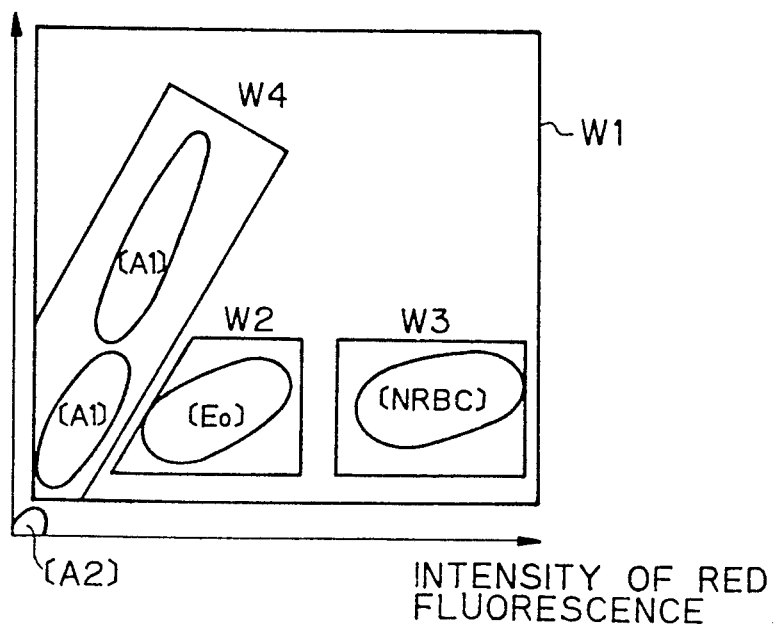
FIG. 4 is a scattergram wherein the intensity of red fluorescence and the intensity of green fluorescence of the specimen obtained in Example 1 are referred to as the coordinate axes.
Figure 5:
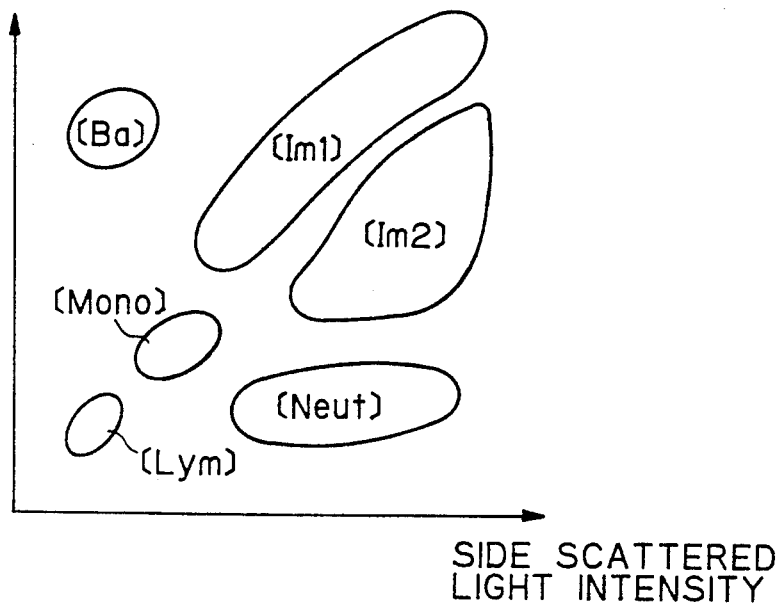
FIG. 5 is a scattergram wherein the side scattered light intensity and the intensity of red or green fluorescence of the data of the subpopulation [A1] in FIG. 4 are referred to as the coordinate axes.

0.90 ml of the first reagent solution of the above Composition Example 1 was mixed with 0.05 ml of peripheral blood containing abnormal cells (erythroblasts and immature granulocytes) and was then allowed to incubate for 5 seconds or longer. Then 0.01 ml of the second reagent solution was further added thereto and the obtained mixture was allowed to incubate for an additional 10 seconds or longer. Thus a speciment to be assayed was obtained. Leukocytes were classified and counted by measuring the red fluorescence, green fluorescence, side scattered light and forward scattered light of each cell with a flow cytometer of FIG. 1. Then a scattergram was formed by referring the intensity of red fluorescence and that of green fluorescence to as the coordinate axes, as shown in FIG. 4. Thus leukocytes were divided into subpopulations, namely, one comprising erythroblasts [NRBC], one comprising eosinophils [Eo], one comprising other leukocytes [A1] and one comprising blood corpuscles other than leukocytes [A2]. Then the whole leukocytes were delineated within a window 1 [W1] and counted. Thus the total leukocyte number was determined. Next, the eosinophils and the erythroblasts were gated respectively with a window 2 [W2] and a window 3 [W3], followed by counting. Other leukocytes were taken out with a window 4 [W4] and a scattergram was formed by referring the side scattered light intensity and the intensity of green or red fluorescence as to the coordinate axes, as shown in FIG. 5. Thus subpopulations involving one comprising lymphocytes [Lym], one comprising monocytes [Mono], one comprising neutrophils [Neut], one comprising immature granulocytes 1 [Im1] and one comprising immature granulocytes 2 [Im2] were obtained. Each of these subpopulations was gated with a window and counted. The value thus obtained was divided with the total leukocyte number determined above. Thus the percentage of each leukocyte type was obtained.

EXAMPLE 2

Composition Example 2

| First reagent solution: | |
| --- | --- |
| Astrazon Yellow 3G | 300 mg |
| Neutral Red | 20 mg |
| ethidium bromide | 50 mg |
| Astrazon Orange R | 300 mg |
| citric acid monohydrate | 2.10 g (pH 2.62) |
| purified water (pH: 2.62, osmotic pressure: about 10 mOsm/kg). | 1 l |
| Second reagent solution: | |
| taurine | 37.5 g |
| NaCl | 58.4 g |
| NaOH | 16.0 g |
| polyoxyethylene cetyl ether | 50 g |

| -continued | |
|---|---|
| purified water | 1 l |

Figure 6:
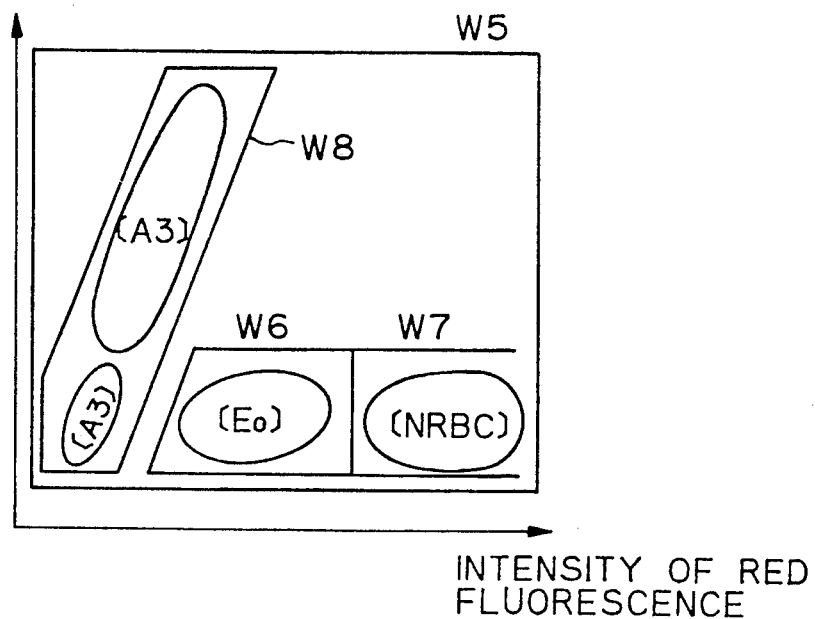
FIG. 6 is a scattergram wherein the intensity of red fluorescence and the intensity of green fluorescence of the specimen obtained in Example 2 are referred to as the coordinate axes.
Figure 7:
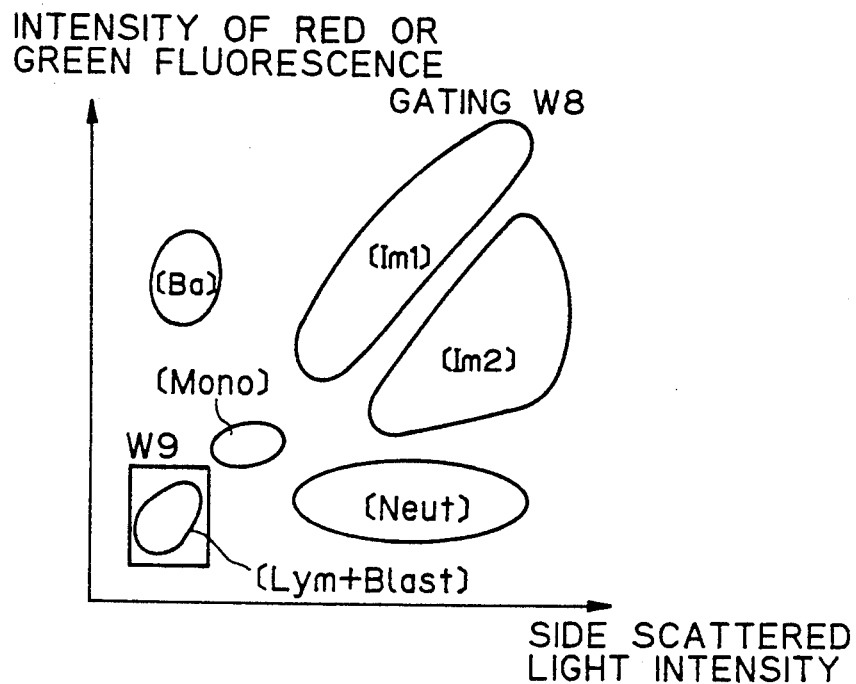
FIG. 7 is a scattergram wherein the side scattered light intensity and the intensity of red or green fluorescence of the data of the subpopulation [A3] in FIG. 6 are referred to as the coordinate axes.
Figure 8:
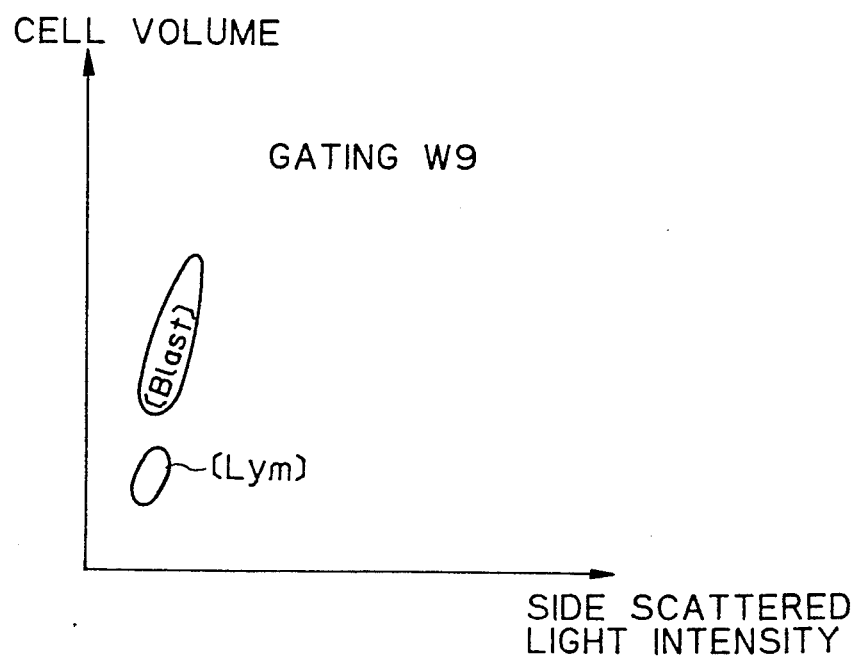
FIG. 8 is a scattergram wherein the side scattered light intensity and the cell volume, measured based on the electric resistance assay system, of the data obtained from window W9 of FIG. 7 are referred to as the coordinate axes.

0.90 ml of the first reagent solution of the above Composition Example 2 was mixed with 0.05 ml of peripheral blood and then allowed to incubate for 5 seconds or longer. Then 0.10 ml of the second reagent solution was further added thereto and the obtained mixture was allowed to incubate for an additional 10 seconds or longer. Thus a specimen to be assayed was obtained. Leukocytes were classified and counted by measuring the red fluorescence, green fluorescence, side scattered light and cell volume of each cell with a flow cytometer provided with an electrical resistance assay system of FIG. 2. Then a scattergram was formed by referring the intensity of red fluorescence and that of green fluorescence to as the coordinate axes, as shown in FIG. 6. Thus leukocytes were divided into subpopulations, namely, one comprising erythroblasts [NRBC], one comprising eosinophils [Eo], one comprising other leukocytes [A3]. Then the whole leukocytes were delineated within a window 5 [W5] and counted. Thus the total leukocyte number was determined. Next, the eosinophils and the erythroblasts were gated respectively with a window 6 [W6] and a window 7 [W7], followed by counting. Other leukocytes were taken out with a window 8 [W8] and a scattergram was formed by referring the side scattered light intensity and the intensity of green or red fluorescence as to the coordinate axes, as shown in FIG. 7. Thus subpopulations involving one comprising lymphocytes and blasts [Lym+Blast], one comprising monocytes [Mono], one comprising neutrophils [Neut], one comprising basophils [Ba], one comprising immature granulocytes 1 [Im1] and one comprising immature granulocytes 2 [Im2] were obtained. Each of these subpopulations was gated with a window and counted. The lymphocytes and blasts were gated with a window 9 [W9] and a scattergram was formed by referring the side scattered light intensity and the cell volume, measured based on the electrical resistance assay principle, to as the coordinate axes, as shown in FIG. 8. Thus two subpopulations, namely, one comprising lymphocytes [Lym] and one comprising blasts [Blast] were observed. Each subpopulation was delineated within a window and counted. The value thus obtained was divided with the total leukocyte number determined above. Thus the percentage of each leukocyte type was obtained.

1. A hematological sample is treated by the method of the present invention and thus a specimen to be assayed by flow cytometry is prepared. Thus immature granulocytes can be specifically stained and separated.

As a result, leukocytes can be divided into at least eight groups simply by measuring a single specimen with a flow cytometer.

2. The measurement with a flow cytometer provided with an electrical resistance assay system further makes it possible to separate blasts.

Thus leukocytes can be divided into at least nine groups simply by measuring a single specimen with a flow cytometer.

What is claimed is:

1. A method for preparing a specimen for classifying and counting blood corpuscles into at least eight groups, namely, two comprising immature granulocytes group 1 and immature granulocytes group 2, one comprising erythroblasts, one comprising basophils, one comprising eosinophils, one comprising lymphocytes, one comprising monocytes and one comprising neutrophils, by assaying a single specimen with a flow cytometer, which comprises the following steps:

(1) a step for eliminating influences of erythrocytes from a hematological sample without changing the leukocytes morphology comprising:
  i) fragmentizing said erythrocytes contained in said hematological sample by adding a first aqueous solution of a low osmotic pressure to said sample to form a mixture, said aqueous solution comprising a buffer for maintaining the mixture within an acidic pH range of the hematological sample and for damaging the cell membranes of erythroblasts only;
  ii) adding to said mixture of hematological sample and first aqueous solution obtained in a second solution comprising an osmolarity compensating agent for maintaining the morphology of leukocytes and a buffer for neutralizing the first aqueous solution and for adjusting the pH to a level suitable for staining; and (2) a step for staining said blood corpuscles contained in said hematological sample with at least four dyes specified below:
  i) Astrazon Yellow 3G capable of differentially staining at least basophils and immature granulocytes;
  ii) Neutral Red capable of differentially staining at least eosinophils;
  iii) a dye capable of differentially staining at least either or both of nuclei and cytoplasm of leukocytes; and
  iv) a fluorochrome capable of staining exclusively nuclei of the damaged erythroblasts.

2. A method according to claim 1, wherein said dye capable of staining at least the nuclei or cytoplasm of leukocytes is at least one dye selected from a group consisting of the following dyes:
  (1) Astrazon Orange R
  (2) Astra Violet
  (3) Rhodamine 6G
  (4) Rhodamine 19
  (5) Rhodamine B
  (6) Rhodamine 3GO
  (7) Pyronine B
  (8) Cyanosine
  (9) 3,3'-dimethylthiocarbocyanine iodide
  (10) 3,3'-diethylthiocarbocyanine iodide
  (11) 3,3'-dipropyloxacarbocyanine iodide
  (12) 3,3'-dihexyloxacarbocyanine iodide
  (13) 3,6-bis(dimethylamino)-10-dodecylacridinium bromide
  (14) 7-benzylamino-4-nitrobenzoxadiazole
  (15) 7-fluoro-4-nitrobenzoxadiazole
  (16) Astrazon Red 6B.

3. A method according to claim 1, wherein said fluorochrome capable of staining exclusively the nuclei of damaged cells is at least one dye selected from a group consisting of the following dyes:
  (1) ethidium bromide
  (2) propidium iodide
  (3) N-methyl-4-(1-pyrene)vinyl-propidium iodide.

4. A method for preparing a specimen for classifying and counting blood corpuscles into at least nine groups, namely, two comprising immature granulocytes group 1 and immature granulocytes group 2, one comprising erythroblasts, one comprising blasts, one comprising basophils, one comprising eosinophils, one comprising lymphocytes, one comprising monocytes and one comprising neutrophils, by assaying a single specimen with a flow cytometer, which comprises the following steps:

(1) a step for eliminating influences of erythrocytes from a hematological sample without changing the leukocytes morphology comprising:
  i) fragmentizing said erythrocytes contained in said hematological sample by adding a first aqueous solution of a low osmotic pressure to said sample to form a mixture, said aqueous solution comprising a buffer for maintaining the mixture within an acidic pH range of the hematological sample and for damaging the cell membranes of erythroblasts only;
  ii) adding to said mixture of hematological sample and first aqueous solution obtained in i) a second solution comprising an osmolarity compensating agent for maintaining the morphology of leukocytes and a buffer for neutralizing the first aqueous solution and for adjusting the pH to a level suitable for staining; and
  iii) lysing the erythrocytes fragmentized in the above i) or ii) with a nonionic surfactant;
  iv) adding a salt, which dissociates into ions in aqueous solutions of said salt to thereby maintain electrical conductivity of such solution at a suitable level, to the specimen to be finally prepared so as to control the electrical conductivity of said specimen to a level suitable for measuring with a device provided with an electrical resistance assay system, thus making it possible to accurately determine cell volume; and (2) a step for staining said blood corpuscles contained in said hematological sample with at least four dyes specified below:
  i) Astrazon Yellow 3G capable of differentially staining at least basophils and immature granulocytes;
  ii) Neutral Red capable of differentially staining at least esoinophils;
  iii) a dye capable of differentially staining at least either or both of nuclei and cytoplasm of leukocytes; and
  iv) a fluorochrome capable of staining exclusively nuclei of the damaged erythroblasts.

5. A method according to claim 4, wherein said nonionic surfactant for lysing the erythrocyte fragments is a surfactant having a hydrophilic group containing polyoxyethylene of a degree of polymerization of 20 or above.

6. A method according to claim 4, wherein said dye capable of staining at least nuclei or cytoplasm of leukocytes is at least one dye selected from a group consisting of the following dyes:
  (1) Astrazon Orange R
  (2) Astra Violet
  (3) Rhodamine 6G
  (4) Rhodamine 19
  (5) Rhodamine B
  (6) Rhodamine 3GO
  (7) Pyronine B
  (8) Cyanosine
  (9) 3,3'-dimethylthiocarbocyanine iodide
  (10) 3,3'-diethylthiocarbocyanine iodide
  (11) 3,3'-dipropyloxacarbocyanine iodide
  (12) 3,3'-dihexyloxacarbocyanine iodide
  (13) 3,6-bis(dimethylamino)-10-dodecylacridinium bromide
  (14) 7-benzylamino-4-nitrobenzoxadiazole
  (15) 7-fluoro-4-nitrobenzoxadiazole
  (16) Astrazon Red 6B.

7. A method according to claim 4, wherein said fluorochrome capable of staining exclusively the nuclei of damaged cells is at least one dye selected from a group consisting of the following dyes:
  (1) ethidium bromide
  (2) propidium iodide
  (3) N-methyl-4-(1-pyrene)vinyl-propidium iodide.

* * * * *